US008334306B2

(12) United States Patent
Ba et al.

(10) Patent No.: US 8,334,306 B2
(45) Date of Patent: *Dec. 18, 2012

(54) NITROXIDE FREE RADICAL SYNERGIZED ANTINEOPLASTIC AGENTS

(75) Inventors: Yong Ba, Monrovia, CA (US); Errol V. Mathias, Alhambra, CA (US)

(73) Assignee: The Trustees of California State University, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/053,170

(22) Filed: Mar. 21, 2011

(65) Prior Publication Data

US 2012/0065230 A1    Mar. 15, 2012

Related U.S. Application Data

(63) Continuation of application No. 11/685,187, filed on Mar. 12, 2007, now Pat. No. 7,910,607.

(60) Provisional application No. 60/781,071, filed on Mar. 10, 2006.

(51) Int. Cl.
   *C07D 215/38*   (2006.01)
   *A61K 31/04*    (2006.01)

(52) U.S. Cl. ......... 514/327; 514/316; 546/222; 546/188

(58) Field of Classification Search .................. 546/222, 546/188; 514/327, 316
   See application file for complete search history.

(56) References Cited

U.S. PATENT DOCUMENTS 7,910,607 B2 *  3/2011  Ba et al. ......................... 514/327
2004/0024025 A1  2/2004  Kasid et al.

OTHER PUBLICATIONS

Suwalsky, M. et al., "The Anticancer Drug Chlorambucil Interacts with the Human Erythrocyte Membrane and Model Phospholipid Bilayers," Zeitschrift fur Naturforschung, 54(12):1089-1095 (1999).
Masta, A. et al., "Nitrogen Mustard Inhibits Transcription and Translation in a Cell Free System," Nucleic Acids Research, 23(17):3508-3515 (1995).
Kohn, K. et al., "Mechanisms of DNA Sequence Selective Alkylation of Guanine-N7 Positions by Nitrogen Mustards," Nucleic Acid Research, 15(24):10531-10549 (1987).
Yang, X. et al., "P-Glycoprotein Expression in Ovarian Cancer Cell Line Following Treatment with Cisplatin," Oncology Research, 7(12):619-24 (1995).
Kundu, G. et al., "The Alkylating Properties of Chlorambucil," Pharmacology Biochemistry and Behavior, 49 (3):621-24 (1994).
Passagne, I. et al., "O6-Methylguanine DNA-methyltransferase (MGMT) Overexpression in Melanoma Cells Induces Resistance to Nitrosoureas and Temozolomide but Sensitizes to Mitomycin C," Toxicology and Applied Pharmacology, 211(2):97-105 (2006).
Munson, A.E. et al., "Synergistic Lethal Action of Alkylating Agents and Sodium Pentobarbital in the Mouse," Pharmacology, 11(4):231-40 (1974).
Gupta, V.S. et al., "Reaction of Bifunctional Alkylating Agents with Tetrahydrofolate," Biochemistry, 6(7):2159-2168 (1967).
Hall, M.D. et al., "Comparative Efficacy of Novel Platinum(IV) Compounds with Established Chemotherapeutic Dugs in Solid Tumour Models," Biochemical Pharmacology, 67:17-30 (2004).
Rad, A.N. et al., "The Differential Influence of Allogeneic Tumor Cell Death via DNA Damage on Dendritic Cell Maturation and Antigen Presentation," Cancer Research 63:5143-5150 (2003).
Pandya, U. et al., "Activity of Allelic Variants of Pi Class Human Glutathione S-transferase Toward Chlorambucil," Biochemical and Biophysical Research Communications 278:258-62 (2000).
Mahoney, B.P. et al., "Tumor Acidity, Ion Trapping and Chemotherapeutics I. Acid pH Affects the Distribution of Chemotherapeutic Agents in vitro," Biochemical Pharmacology 66:1207-1218 (2003).
Helliger, W. et al., "Differential Sensitivity of Histone Acetylation in Nitrogen-Mustard Sensitive and Resistant Cells. Relation to Drug Uptake, Formation and Repair of DNA-interstrand Cross-links," Eur J Cancer Clin Oncol 24 (12):1861-1868 (1988).
Lee, M. et al., "Design, Synthesis and Biological Evaluation of DNA Sequence and Minor Groove Selective Alkylating Agents," Anti-Cancer Drug Design, 8:173-192 (1993).
Sladek, N.E., "Cytotoxic Activity of Alkylating Agents in the Presence of Centrophenoxine and its Hydrolysis Products," Journal of Pharmacology and Experimental Therapeutics, 203(3):630-639 (1977).
Poot, M. et al., "Cytostatic Synergism Between Bromodeoxyuridine, Bleomycin, Cisplatin and Chlorambucil Demonstrated by a Sensitive Cell Kinetic Assay," Biochemical Pharmacology, 41(12):1903-1909 (1991).
Zhang, J. et al., "Metabolism of Chlorambucil by Rat Liver Microsomal Glutathione S0transferase," Chemico-Biological Interactions, 149:61-67 (2004).
Hall, A.G. et al., "Mechanism of Action of, and Modes of Resistance to, Alkylating Agents Used in the Treatment of Haematological Malignancies," Blood Reviews, 6:163-173 (1992).
Mattes, W.B. et al., "GC-rich Regions in Genomes as Targets for DNA Alkylation," Carcinogenesis, 9(11):2065-2072 (1988).
Bishop, J.B. et al., "Alterations in the Reproductive Patterns of Female Mice Exposed to Xenobiotics," Fundamental and Applied Toxicology, 40:191-204 (1997).
Van Putten, L.M. et al., "Factors Determining Cell Killing by Chemotherapeutic Agents in vivo—II. Melphalan, Chlorambucil and Nitorgen Mustard," Europ J Cancer 7:11-16 (1970).
Bramson, J. et al., "Nitrogen Mustard Drug Resistance B-cell Chronic Lymphocytic Leukemia as an in vivo Model for Crosslinking Agent Resistance," Mutation Research, 336:269-78 (1995).
Drablos, F. et al., "Alkylation Damage in DNA and RNA—Repair Mechanisms and Medical Significance," DNA Repair 3:1389-1407 (2004).

(Continued)

*Primary Examiner* — D M Seaman

(74) *Attorney, Agent, or Firm* — Mastermind IP Law P.C.; Diane L. Gardner

(57) ABSTRACT

Nitroxide free radicals attached to antineoplastic agents can synergize their potencies to cancer cells. This invention relates to any antineoplastic agents and their derivatives chemically attached with nitroxide free radicals, such as TEMPO and its radical derivatives. This invention also relates to precursors of such compounds, as well as the products formed from the adducts after administration.

6 Claims, No Drawings

OTHER PUBLICATIONS

Vogel, E.W. et al., "Heritable and Cancer Risks of exposures to Anticancer Drugs: Inter-species Comparisons of Covalent Deoxyribonucleic Acid-binding Agents," Mutation Research 400:509-540 (1998).

Shinohara, K. et al., "Mechanism of Inhibition of Red Blood Cell Glutathione Reductase Activity by BCNU (1,3-bis(2-chloroethyl)-1-Nitrosourea)," Clinica Chimica Acta 92:147-152 (1979).

Grunicke, H. et al., "Plasma Membrane as Target of Alkylating Agents," Advances in Enzyme Regulation, 24:247-61 (1985).

Lewis, F.B. et al., "X-radiation and Alkylating Agents as Possible 'Trigger' Mechanisms in the Autoimmune Complications of Malignant Lymphoproliferative Disease," Clin Exp Immunol 1:3-11 (1966).

Johnston, J.B. et al., "Role of the TRAIL/APO2-L Death Receptors in Chlorambucil and Fludarabine-induced Apoptosis in Chronic Lymphocytic Leukemia," Oncogene, 22:8356-69 (2003).

Singer, M.J. et al., "Targeted Mutagenesis of DNA with Alkylating RecA Assisted Oligonucleotides," Nucleic Acids Research, 27(24):e38i-viii (1999).

Bosanquet, A.G. et al., "Novel ex vivo Analysis of Nonclassical, Pleiotropic Drug Resistance and Collateral Sensitivity Induced by Therapy Provides a Rationale for Treatment Strategies in Chronic Lymphocytic Leukemia," Blood, 87(5):1962-1971 (1996).

Christodoulopoulos, G. et al., "Potentiation of Chlorambucil Cytotoxicity in B-cell Chronic Lymphocytic Leukemia by Inhibition of DNA-dependent Protein Kinase Activity Using Wortmannin," Cancer Research 58(9):1789-92 (1998).

Ioannidou, E. et al., "Synergistic Induction of Cytogenic Damage by Alkylating Antineoplastics and 5-Azacytidine in Human Lymphocytes," Environmental and Molecular Mutagenesis, 14:6-12 (1989).

Harrap, K.R. et al., "The Alkylating Agent: Does a Knowledge of its Mode of Action Suggest Leads for Improving its Therapeutic Effectiveness?" Excerpta Medica International, 375:106-121 (1975).

Lohman, P.H.M., "Qualitative and Quantitative Procedures for Health Risk Assessment," Mutation Research, 428:237-54 (1999).

Cruciani, G. et al., "Structure-based Rationalization of Antitumor Drugs Mechanism of Action by a MIF Approach," European Journal of Medicinal Chemistry, 39:281-89 (2004).

Khan, S. et al., "Hepatocyte Toxicity of Mechlorethamine and Other Alkylating Anticancer Drugs," Biochemical Pharmacology, 43(9): 1963-67 (1992).

Monti, E. et al., "Nitroxide TEMPOL Impairs Mitochondrial Function and Induces Apoptosis in HL60 Cells," Journal of Cellular Biochemistry, 82:271-276 (2001).

Pietschmann, C., "Antibodies as Selective Weapons," Livingbridges, 1:54-57 (2001).

Namiecinski, M. et al., "Cytotoxicity, Cytoprotection and Neurotoxicity of Novel Deprenyl-related Propargylamines, Stable Nitroxide Free Radicals, in vitro and in vivo," In Vivo, 18(2):171-80 (2004)—Abstract.

Wu, Y. et al., "Cytotoxicity of a Newly Synthesized Nitroxide Derivative of 4-ferrocenecarboxyl-2,2,6,6-tetramethylpiperidine-1-oxyl in High Metastatic Lung Tumor Cells," Pharmazie, 61(12):1028-33 (2006).

* cited by examiner

NITROXIDE FREE RADICAL SYNERGIZED ANTINEOPLASTIC AGENTS

This application claims priority from U.S. Provisional Patent Application No. 60/781,071, filed on Mar. 10, 2006, incorporated herein by reference.

The inventors acknowledge U.S. National Science Foundation grant no. 0351848, under which the U.S. Federal Government has a non-exclusive, non-transferable, irrevocable, paid-up license to practice this invention on behalf of the United States.

BACKGROUND

TEMPO (2,2,6,6-Tetramethylpiperidine-1-oxyl) is widely used as a radical trap, as a structural probe for biological systems in conjunction with electron spin resonance (ESR) or electron paramagnetic resonance (EPR) spectroscopy, as a reagent in organic synthesis, and as an initiator in polymer chemistry. Several derivatives of TEMPO are known. For example, TEMPOL (4-hydroxy-2,2,6,6-tetramethylpiperidine-N-oxyl) is a stable, cell-permeable nitroxide free radical that acts as a radical scavenger and nitric oxide spin trap. TEMPOL is known to impair mitochondrial function and induce apoptosis in a number of tumor cell lines through free radical dependent mechanisms. TEMPO and its derivatives may exert cyto-protective or cyto-toxic effects. Such dual behavior is common among antioxidants. Recently, TEMPO has been suggested for co-administration with other anti-cancer drugs.

SUMMARY OF THE INVENTION

We have synthesized a new compound, chlorambucil-TEMPOL adduct, obtained through covalently bonding TEMPOL to chlorambucil through an esterification process. Surprisingly, we found that the adduct has higher potency than mere co-administration of the two drugs. Without wishing to be bound by theory, it is believed that the increased activity is the product of the proximity of the active sites of both compounds, which were left intact in the adduct. Therefore, similar syntheses can be performed to create highly potent adduct compounds from other anticancer agents, using the appropriate TEMPO derivative. We anticipate broadly that nitroxide free radicals attached to antineoplastic agents can synergize their potencies to cancer cells. This invention relates to any antineoplastic agents and their derivatives chemically attached with nitroxide free radicals, such as TEMPO and its radical derivatives. This invention also relates to precursors of such compounds, as well as the products formed from the adducts after administration.

DETAILED DESCRIPTION

Throughout this specification, the terms "a" and "an" and variations thereof represent the phrase "at least one." In all cases, the terms "comprising", "comprises" and any variations thereof should not be interpreted as being limitative to the elements listed thereafter. Unless otherwise specified in the description, all words used herein carry their common meaning as understood by a person having ordinary skill in the art. In cases where examples are listed, it is to be understood that combinations of any of the alternative examples are also envisioned. The scope of the invention is not to be limited to the particular embodiments disclosed herein, which serve merely as examples representative of the limitations recited in the issued claims resulting from this application, and the equivalents of those limitations.

Alkylating agents are potent therapeutics useful for treating a wide variety of cancers. Alkylation of DNA results in breaks in the DNA molecule, as well as cross-linking of the twin strands, thus interfering with DNA replication and transcription of RNA. Chlorambucil is an important anticancer drug used in chemotherapy to treat different types of cancers due to the effect of its N,N-bis-(2-chlorethyl) amino residue on DNA alkylation. Chlorambucil is used in chemotherapy to treat chronic lymphocytic leukemia, giant follicular lymphoma, and Hodgkin's disease. It is also an immunosuppressive agent that has been used to treat systemic lupus erythematosus, Waldenström's macroglobulinemia, and glomerular nephritis. Other alkylating agents useful for this invention include, but are not limited to cyclophosphamide, uracil mustard, L-phenylalanine mustard (Melphalan), 1,3-bis(2-chloroethyl)-1-nitrosourea (carmustine), streptozotocin, dacarbazine, and temozolomide.

It should be appreciated that other anticancer agents are also contemplated as being useful for preparing TEMPO or TEMPO derivative adduct compounds. Examples include, but are not limited to anthracyclines such as doxorubicin, daunorubicin and idarubicin, antimetabolites such as flourouracil and its derivatives, and hydroxyurea.

TEMPO is a stable nitroxide free radical that is shown to have antioxidant catalytic activity which mimics those of superoxide dismutase (SOD), and which when existing in vivo, can interact with other substances to perform catalase-mimic activity. The molecular structure of TEMPO is

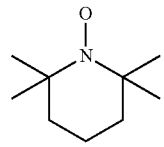

In the past, nitroxides including TEMPO, have been used in electron spin resonance spectroscopy as "spin labels" for studying conformational and motional characteristics of biomacromolecules. Nitroxides have also been used to detect reactive free radical intermediates because their chemical structure provides a stable unpaired electron with well defined hyperfine interactions. In addition, nitroxides have been observed to act as enzyme mimics; certain low molecular weight nitroxides have been identified to mimic the activity of superoxide dismutase. Numerous studies also show that nitroxides that are permeable to cell membranes are capable of short-term protection of mammalian cells against cytotoxicity from superoxide anion generated by hypoxantine/xanthine oxidase and from hydrogen peroxide exposure. The term "TEMPO" is meant to include the stable nitroxide free radical, its precursors and its natural and synthetic derivatives. Examples of derivatives of TEMPO include, but are not limited to 4-hydroxy-TEMPO (TEMPOL), 4-amino-TEMPO, 4-carboxy-TEMPO, 4-acetamido-TEMPO and 4-bromo-TEMPO.

TEMPOL is the 4-hydroxy derivative of TEMPO and is widely used as a spin labeling agent for EPR studies in biological systems. TEMPOL has two reaction sites with OH at the 4-position of the piperidine ring, and the nitroxyl group.

In a preferred embodiment, a chlorambucil-TEMPOL adduct is synthesized by the following reaction:

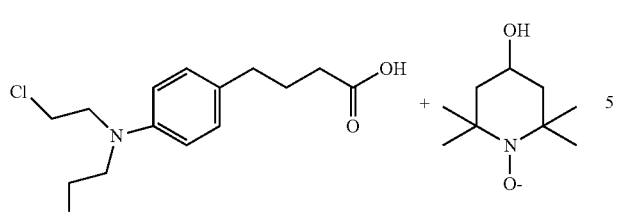 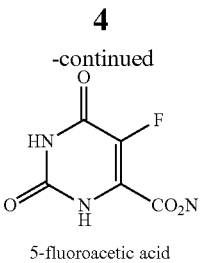

CHLORAMBUCIL  TEMPOL

DCC
DMAP

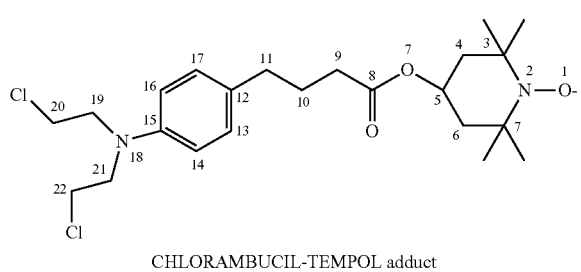

CHLORAMBUCIL-TEMPOL adduct

Other drugs can be similarly synthesized. For example, the —NH group present in cyclophosphamide

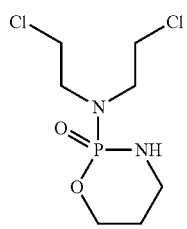

can react with TEMPOL or its derivative, such as 4-carboxy-TEMPO. The same reaction can be used to react with the —NH group in uracil mustard

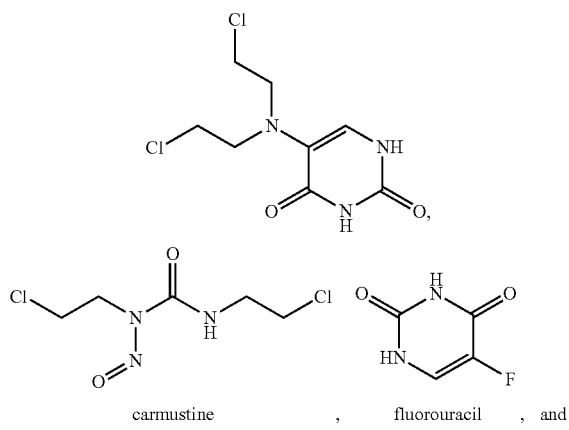

carmustine, fluorouracil, and

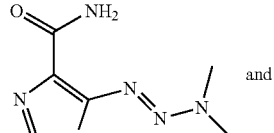

5-fluoroacetic acid with the reaction to the carboxylic group, too.

In another example, the —NH$_2$ functional group

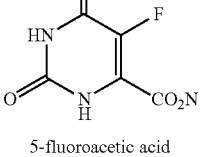

in dacarbazine and

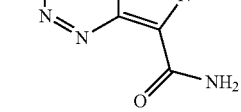

in temozolomide may be employed in the reaction.

Some drugs may have more than one appropriate functional group, creating the possibility for several different new compounds depending upon which reaction/functional group is/are employed. In one embodiment, a synthesis may be conducted whereby multiple bonds are created with TEMPO or its derivatives, where the TEMPO or derivative used may be the same or different. For example,

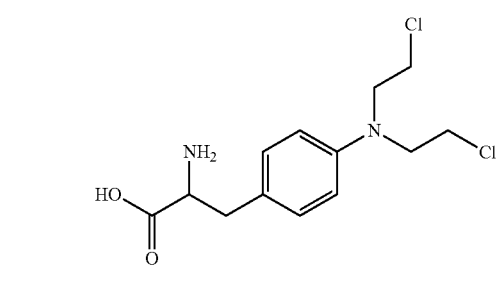

Melphalan has both —NH$_2$ and —COOH functional groups available for binding two TEMPO derivatives to the drug molecule.

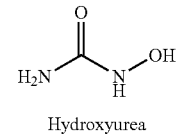

Hydroxyurea also has multiple functional groups.

For anticancer drugs containing —OH group, the same reaction can be carried out using

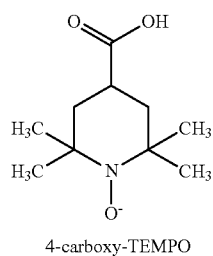

4-carboxy-TEMPO or a derivative thereof.
For example,

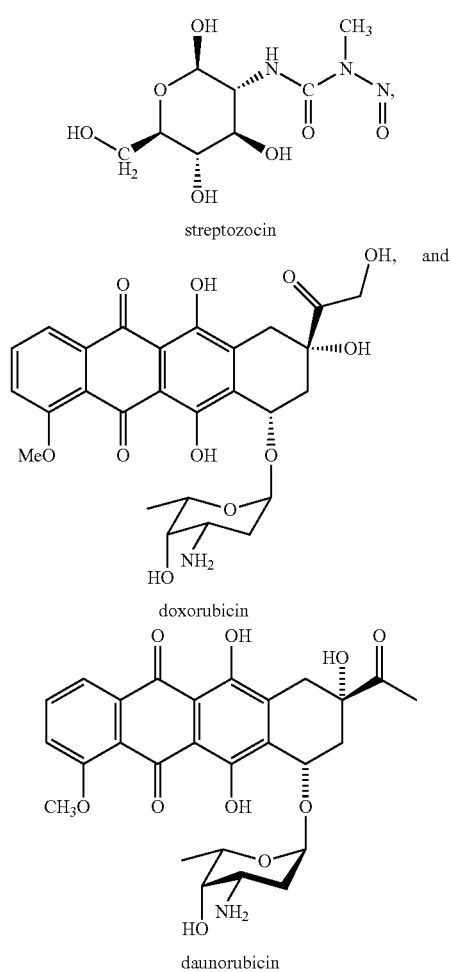

each contain multi-terminal —OH groups.

Based upon this disclosure, any person having ordinary skill in the art could determine antineoplastic agents having suitable functional groups that could be covalently bound to TEMPO or its precursors or derivatives to create new compounds contemplated by the inventors. The novel compounds of this invention may be used to make new pharmaceutical compositions useful for treating a wide variety of cancers, readily apparent to those persons having ordinary skill in the art.

In the case where —NH or —OH groups are present in the drugs, any reacting TEMPO derivative (R-TEMPO) can be used to carry out the reaction. R in some cases can be —COOH, —Br, anhydride, or any reactive functional group in TEMPO which can attack the —NH or —OH functional group of the parent moiety. In the case where two or more functional groups are present in the parent molecule, a mixture of R-TEMPO adducts can be formed. The number of compounds in such a mixture is not limited to the number of functional groups present in the parent drug molecule. We have illustrated two possible compounds in some of the following examples. In the case where —COOH functional groups are present in the parent molecule, it is preferable that the reaction be performed with TEMPOL, although any derivative of TEMPO can be used.

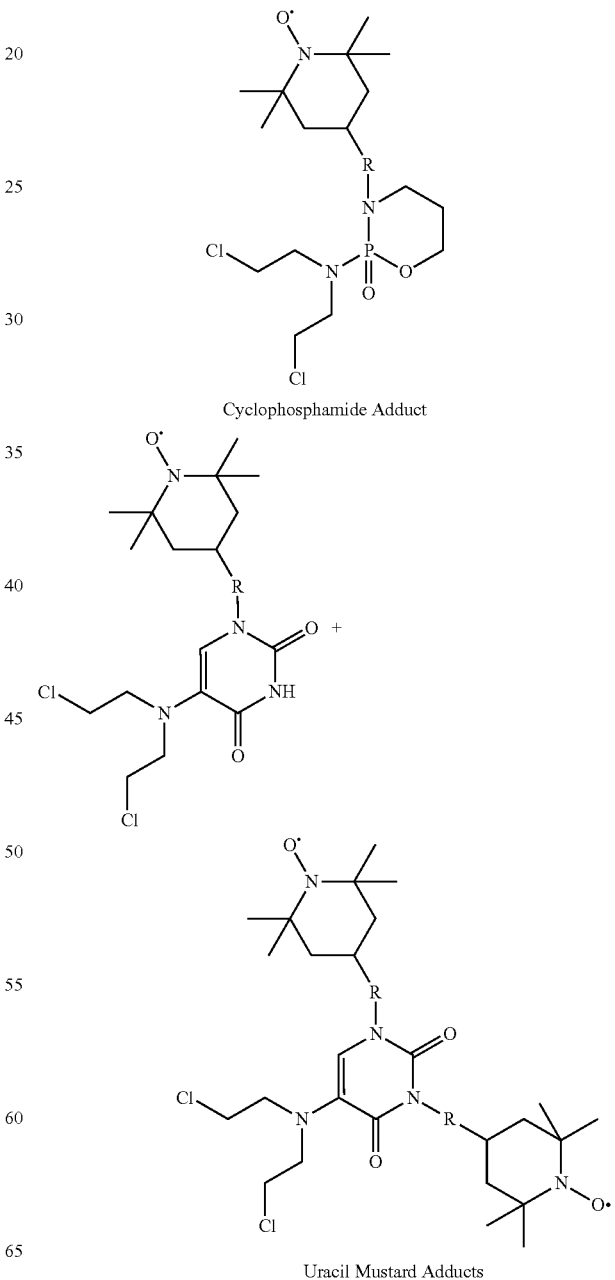

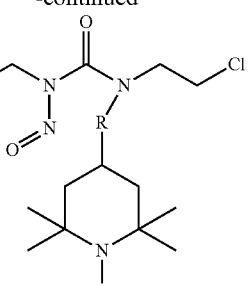
Carmustine Adduct
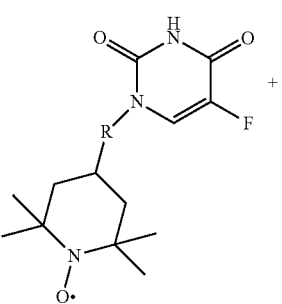
+
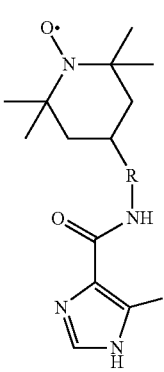
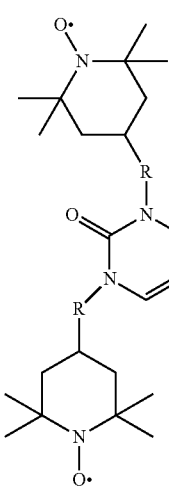
5-fluorouracil Adducts
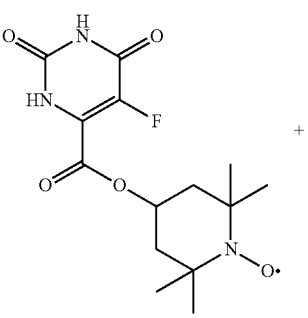
+
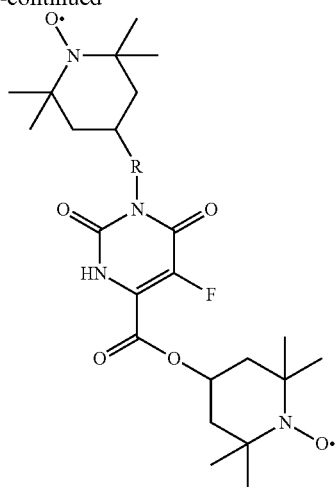
5-fluoroacetic acid Adducts
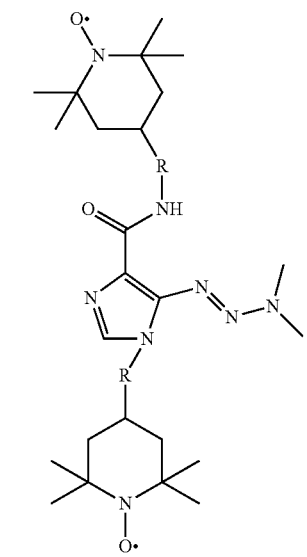
Dacarbazine Adducts

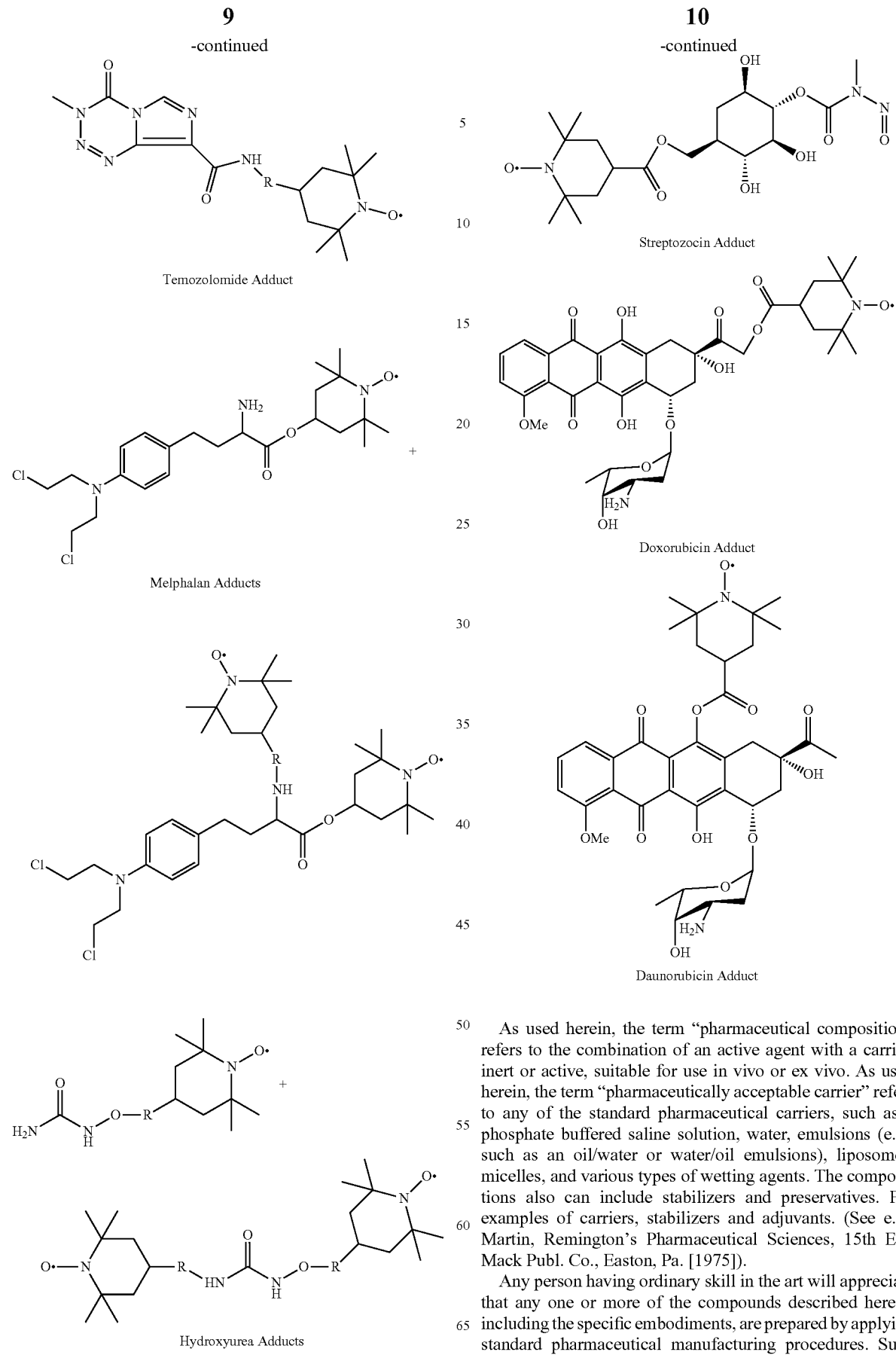

As used herein, the term "pharmaceutical composition" refers to the combination of an active agent with a carrier, inert or active, suitable for use in vivo or ex vivo. As used herein, the term "pharmaceutically acceptable carrier" refers to any of the standard pharmaceutical carriers, such as a phosphate buffered saline solution, water, emulsions (e.g., such as an oil/water or water/oil emulsions), liposomes, micelles, and various types of wetting agents. The compositions also can include stabilizers and preservatives. For examples of carriers, stabilizers and adjuvants. (See e.g., Martin, Remington's Pharmaceutical Sciences, 15th Ed., Mack Publ. Co., Easton, Pa. [1975]).

Any person having ordinary skill in the art will appreciate that any one or more of the compounds described herein, including the specific embodiments, are prepared by applying standard pharmaceutical manufacturing procedures. Such medicaments can be delivered to the subject by using delivery methods that are well-known in the pharmaceutical arts. The compositions may include one or more pharmaceutically acceptable carriers and optionally other therapeutic agents. Each carrier must be "acceptable" in the sense that it is compatible with the other ingredients of the formulation and not injurious to the subject.

Contemplated formulations include those suitable oral, rectal, nasal, topical (including transdermal, buccal and sublingual), vaginal, parenteral (including subcutaneous, intramuscular, intravenous and intradermal) and pulmonary administration. In some embodiments, formulations are conveniently presented in unit dosage form and are prepared by any method known in the art of pharmacy. Such methods include the step of bringing into association the active ingredient with the carrier which constitutes one or more accessory ingredients. In general, the formulations are prepared by uniformly and intimately bringing into association (e.g., mixing) the active ingredient with liquid carriers or finely divided solid carriers or both, and then if necessary shaping the product.

Formulations of the present invention suitable for oral administration may be presented as discrete units such as capsules, cachets or tablets, wherein each preferably contains a predetermined amount of the active ingredient; as a powder or granules; as a solution or suspension in an aqueous or non-aqueous liquid; or as an oil-in-water liquid emulsion or a water-in-oil liquid emulsion. In other embodiments, the active ingredient is presented as a bolus, electuary, or paste, etc.

In some embodiments, tablets comprise at least one active ingredient and optionally one or more accessory agents/carriers are made by compressing or molding the respective agents. Compressed tablets are prepared by compressing in a suitable machine the active ingredient in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) surface-active or dispersing agent. Molded tablets are made by molding in a suitable machine a mixture of the powdered compound (e.g., active ingredient) moistened with an inert liquid diluent. Tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Pharmaceutical compositions for topical administration according to the present invention are optionally formulated as ointments, creams, suspensions, lotions, powders, solutions, pastes, gels, sprays, aerosols or oils. In alternative embodiments, topical formulations comprise patches or dressings such as a bandage or adhesive plasters impregnated with active ingredient(s), and optionally one or more excipients or diluents.

In preferred embodiments, the topical formulations include a compound(s) that enhances absorption or penetration of the active agent(s) through the skin or other affected areas.

If desired, the aqueous phase of a cream base includes, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof.

In some embodiments, oily phase emulsions of this invention are constituted from known ingredients in a known manner. This phase typically comprises a lone emulsifier (otherwise known as an emulgent), it is also desirable in some embodiments for this phase to further comprises a mixture of at least one emulsifier with a fat or an oil or with both a fat and an oil.

Preferably, a hydrophilic emulsifier is included together with a lipophilic emulsifier so as to act as a stabilizer. It some embodiments it is also preferable to include both an oil and a fat. Together, the emulsifier(s) with or without stabilizer(s) make up the so-called emulsifying wax, and the wax together with the oil and/or fat make up the so-called emulsifying ointment base which forms the oily dispersed phase of the cream formulations.

The choice of suitable oils or fats for the formulation is based on achieving the desired properties (e.g., cosmetic properties), since the solubility of the active compound/agent in most oils likely to be used in pharmaceutical emulsion formulations is very low. Thus creams should preferably be a non-greasy, non-staining and washable products with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the agent.

Formulations for rectal administration may be presented as a suppository with suitable base comprising, for example, cocoa butter or a salicylate. Formulations suitable for vaginal administration may be presented as pessaries, creams, gels, pastes, foams or spray formulations containing in addition to the agent, such carriers as are known in the art to be appropriate.

Formulations suitable for nasal administration, wherein the carrier is a solid, include coarse powders having a particle size, for example, in the range of about 20 to about 500 microns which are administered in the manner in which snuff is taken, i.e., by rapid inhalation (e.g., forced) through the nasal passage from a container of the powder held close up to the nose. Other suitable formulations wherein the carrier is a liquid for administration include, but are not limited to, nasal sprays, drops, or aerosols by nebulizer, and include aqueous or oily solutions of the agents.

Formulations suitable for parenteral administration include aqueous and non-aqueous isotonic sterile injection solutions which may contain antioxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the compound to blood components or one or more organs. In some embodiments, the formulations are presented/formulated in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit, daily sub-dose, as herein above-recited, or an appropriate fraction thereof, of an agent.

It should be understood that in addition to the ingredients particularly mentioned above, the formulations of this invention may include other agents conventional in the art having regard to the type of formulation in question, for example, those suitable for oral administration may include such further agents as sweeteners, thickeners and flavoring agents. It also is intended that the agents, compositions and methods of this invention be combined with other suitable compositions and therapies. Still other formulations optionally include food additives (suitable sweeteners, flavorings, colorings, etc.), phytonutrients (e.g., flax seed oil), minerals (e.g., Ca, Fe, K, etc.), vitamins, and other acceptable compositions (e.g., conjugated linoleic acid), extenders, and stabilizers, etc.

Various delivery systems are known and can be used to administer a therapeutic agent of the present invention, e.g., encapsulation in liposomes, microparticles, microcapsules, receptor-mediated endocytosis, and the like. Methods of delivery include, but are not limited to, intra-arterial, intramuscular, intravenous, intranasal, and oral routes. In specific embodiments, it may be desirable to administer the pharmaceutical compositions of the invention locally to the area in need of treatment; this may be achieved by, for example, and not by way of limitation, local infusion during surgery, injection, or by means of a catheter.

Therapeutic amounts are empirically determined and vary with the pathology being treated, the subject being treated and the efficacy and toxicity of the agent. In some embodiments, in vivo administration is effected in one dose, continuously or intermittently throughout the course of treatment. Methods of determining the most effective means and dosage of administration are well known to those having ordinary skill in the art and vary with the composition used for therapy, the purpose of the therapy, the target cell being treated, and the subject being treated. Single or multiple administrations are carried out with the dose level and pattern being selected by the treating physician. Ideally, the agent should be administered to achieve peak concentrations of the active compound at sites of disease.

Example 1

Synthesis of Chlorambucil-TEMPOL Adduct

DCC coupling reaction was used to couple the carboxylic group of chlorambucil with the hydroxyl group of TEMPOL with the loss of a water molecule. To a stirred solution of TEMPOL (0.172 g, 1 mmol) and chlorambucil (0.304 g, 1 mmol) in methylene chloride (5 ml) at 0° C. under argon, DCC (0.206 g, 1 mmol) (Dicyclohexyl carbodiimide) and DMAP (0.0307 g, 0.25 mmol) (Dimethyl amino pyridine) were added and the reaction mixture was stirred, for 12 hrs at room temperature. The solid materials formed were filtered off, and the filtrate was washed with 1 M HCl (1 ml) followed by saturated NaHCO$_3$ (2 ml) and brine (2 ml). The organic phase was dried over MgSO$_4$ and evaporated in vacuum to give 0.4 g of CT corresponding to a yield of 87%. TLC (Thin Layer Chromatography) of the product showed a single spot only.

Example 2

Mechanistic Route of Synthesis of Chlorambucil-TEMPOL Adduct

Dicyclohexylcarbodiimide (DCC) is used to activate the carboxylic acid. Electrons between carbon nitrogen double bond get pushed on nitrogen making carbon electrophilic, hence oxygen donates its electrons towards electrophilic carbon and in turn itself acquires positive charge and nitrogen acquires negative charge. Negatively charged nitrogen abstracts proton on the oxygen atom. Electrons of carbon oxygen double bond of carboxylic group of chlorambucil get pushed on oxygen and alcohol that is TEMPOL gets attached to the carboxylic carbon by donating electron from oxygen. Electrons from oxygen resonate back on the carbon causing departure of oxygen atoms with its electrons, hence giving cyclohexyl urea as a bi-product, as seen in the following schematic:

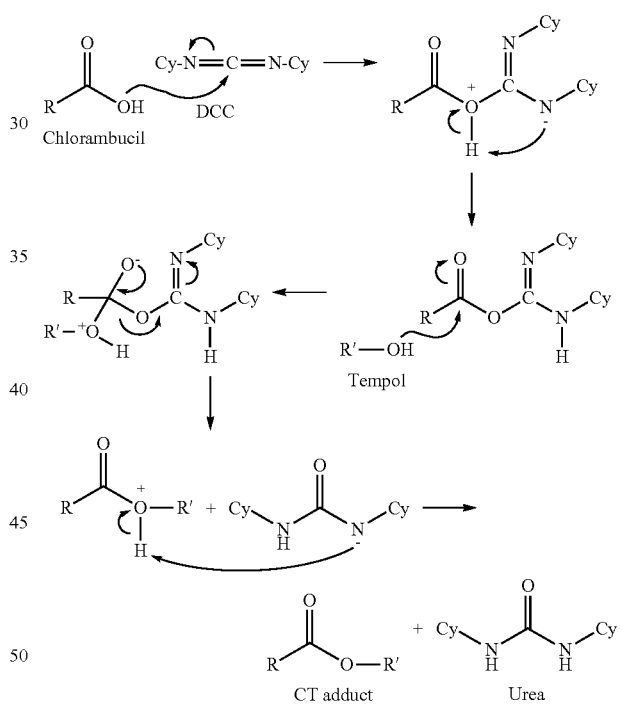

Example 3

Synthesis of Reduced Chlorambucil-TEMPOL Adduct

In order to characterize the structure of the chlorambucil-TEMPOL adduct by using NMR spectroscopy, the nitroxyl free radical was reduced using isoascorbic acid. 3.4 mmol of the product was dissolved in 15 ml of ethanol and 4.8 mmol of isoascorbic dissolved in 1 ml H$_2$O was then added to the solution. Reduction of the nitroxyl group to the hydroxyl was monitored by the disappearance of the pink color in the solution. The solution was then Rotovapped to remove excess solvent and extracted with ether. The organic phase was dried over MgSO$_4$ and evaporated to get the reduced product (1-hydroxy2,2,6,6-tetramethylpiperidin-4-yl-{4-[bis (2-Chloroethyl) amino]phenyl}butanoate) with 95% yield. The reduction of nitroxyl radical is illustrated as follows:

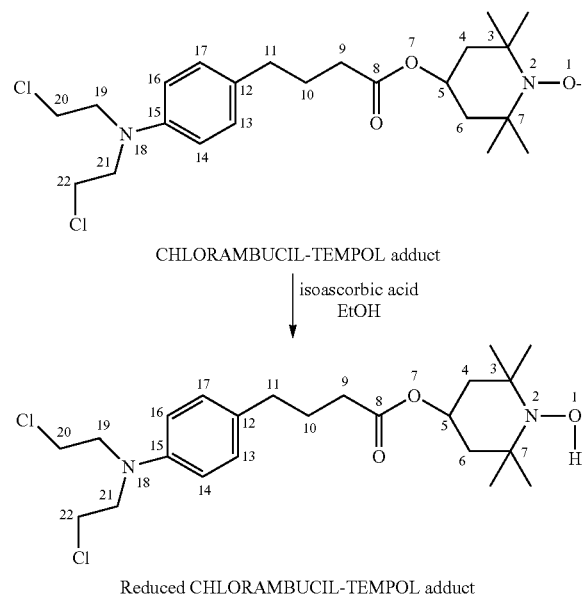

CHLORAMBUCIL-TEMPOL adduct isoascorbic acid
EtOH

Reduced CHLORAMBUCIL-TEMPOL adduct

Example 4

Characterization of Chlorambucil-TEMPOL Adduct—EPR

On completion of synthesis, chlorambucil-TEMPOL was characterized by using modern analytical techniques such as NMR spectroscopy, EPR spectroscopy, Mass spectroscopy, and HPLC. The EPR spectrum was done on a Bruker EMX X-band EPR spectrometer with the results shown in Appendix 1-1. The operating frequency of the spectrometer 9.7 GHz. Typical scans included 20 scans at a center field of 3490 G and a sweep width of 100 G. The TEMPOL and chlorambucil-TEMPOL samples were analyzed at concentrations of $2 \times 10^{-6}$M in methylene chloride solvent. The free radical group was left intact as the compound showed a hyperfine triplet in the EPR spectrum. This hyperfine triplet is characteristic for the TEMPOL free radical as shown in Appendix 1-2.

Example 5

Characterization of Chlorambucil-TEMPOL Adduct—NMR

This being a novel product, complete characterization of the product was needed. The presence of the free radical in the product does not permit the analysis of the product by NMR spectroscopy. Thus, in order to measure the NMR signals for this molecule we had to reduce the nitroxyl group to its corresponding hydroxyl. This was achieved by reducing it with isoascorbic acid as shown in Example 3. The NMR spectrum of chlorambucil-TEMPOL adduct was carried out on a Bruker Avance 400 MHz instrument equipped with a 5 mm QNP probe tuned to proton. Initial recycling delay time of 8 s was used. Typically, 32 scans were carried out. The $^1$H chemical shifts were referenced with TMS (tetramethylsilane) solvent at 0 ppm. The results are shown in Appendix 1-3. All the peaks for the product are visible with a slight trace of impurity; proton signal of the reduced nitroxyl radical appears as a broad hump between 8 to 10 ppm. The peaks belonging to the chlorambucil moiety of the adduct are well characterized with the para substituted aromatic protons appearing in the region between 6.5 to 7.03 ppm. The dimethyl groups of TEMPOL appear together as a singlet at 1.3 ppm and the methylene groups at 1.75-2.07 ppm, the N,N-diethyl chloride peaks in the region between 3.5 and 3.7 ppm and the peaks belonging to the butanoic acid chain in the region of 1.75-1.93 and 2.2-2.5 ppm, as indicated in the following table.

| Chemical shifts in ppm of the Chlorambucil-TEMPOL adduct with in multiplicities parenthesis. | |
|---|---|
| Chemical shift –δ ppm | Assignment of attached protons |
| 1.3 (s) | Dimethyl groups on C3 and C7 |
| 1.75-1.93 (m) | C10 |
| 1.95-2.07 and 1.75-1.93 (m) | C4, and C6 |
| 2.2-2.3 (t) | C11 |
| 2.4-2.5 (t) | C9 |
| 3.5-3.7 (m) | C19, C20, C21, and C22 |
| 5.0-5.1 (m) | C5 |
| 6.5-6.6 (d) | C14, and C16 |
| 6.95-7.03 (d) | C13, and C17 |
| 8.0-10.0 (s) | O1 |

Example 6

Characterization of Chlorambucil-TEMPOL Adduct—Mass Spect

In order to fully characterize the molecule Maldi-TOF mass spectrometry was carried out. Maldi TOF being a soft ionization technique shows the mass peak of the compound as an m/z ratio. In addition to the mass peaks of the sample, peaks of the matrix and daughter ions are also present. Thus, the Maldi-TOF for the product shows an m/z of 458.387, which is the mass of the chlorambucil-TEMPOL, adduct. The mass spectra were analyzed on an Applied Biosystems Voyager System 4397 mass spectrometer. The matrix was 2,5 dihydroxy benzoic acid. A positive reflector mode of operation was used with a N$_2$ laser of 2300 intensity. A blank spectrum to identify the matrix peaks was also carried out. The sample was prepared with the concentration of 100 pmol/μl with the matrix of 10 mg/ml. The results are shown in Appendix 1-4.

Example 7

Characterization of Chlorambucil-TEMPOL Adduct—HPLC

HPLC analysis for the chlorambucil-TEMPOL adduct related samples were carried out on a Waters 600 HPLC system equipped with a Waters 717 plus Autosampler and a waters PDA (photo diode array) detector. The eluents were scanned from 210 nm to 400 nm on the PDA detector and the chromatograms were analyzed at 254 nm that was found to be the most common for the starting materials and the product. The column used was a Supelco Discovery C18 (250 mm×4.6 mm×5 um) reversed phase column. Typically 10 ul of the sample (1000 ppm: 1 mg in 1 ml solvent) dissolved in acetonitrile of HPLC grade was used. Water and Acetonitrile both of HPLC grade were used as the solvent system. The mobile phase was initially maintained at 100% of water. This composition was slowly changed to 100% of Acetonitrile in 20 min. Further, the composition of the mobile phase was maintained for an additional 15 min at 100% acetonitrile giving a total of 35 min for the analysis time. The flow rate for the analysis was maintained at 1 ml/min. Empower 2 software was used to control the system and analyze the chromatogram. In order to analyze the product we had to develop a method to separate the starting materials and the product. Therefore the main starting materials, TEMPOL and chlorambucil had to be injected first and their retention times recorded. The retention time for TEMPOL was found to be 16.96 min, and that for chlorambucil 25.28 min, as shown in Appendix 1-5. Upon analysis of the chlorambucil-TEMPOL product the main peak appeared at a retention time of 27.68 min. as shown in Appendix 1-5. This retention time is quite close to the chlorambucil retention time and hence in order to validate our method a co-injection of 35% chlorambucil and 65% chlorambucil-TEMPOL adduct was prepared. The chromatogram in Appendix 1-6 showed the two peaks at their respective retention times thus validating our HPLC method. The HPLC purity for CT was found to be 85.25% with chlorambucil being the major impurity of 6.01%. Thus the HPLC analysis of the chlorambucil-TEMPOL adduct proves the formation of adduct and confirms our synthesis route.

Example 8

Cytotoxicity Assay

Cells and Cell Culture

MCF-7, human breast cancer cells and KB, human liver cancer cells were maintained in an RPMI 1640 medium, which was supplemented with 10% (v/v) heat-inactivated FBS and 1% (v/v) penicillin-streptomycin (100 U/mL penicillin G and 100 µg/mL streptomycin). The cells were incubated and then allowed to grow into a monolayer at a Petri dish at 37° C. in 5% $CO_2$ and 90% relative humidity. The cells were detached by trypsinisation. Specifically, to detach the monolayer of cells, the medium was removed from the cell culture dish and the cells were washed by PBS buffer solution. Then 1 mL of the enzyme of trypsin was transferred to the cell dish and then the dish was incubated for 3 min. After the incubation, we transferred 4 mL of the RPMI 1640 medium to the cell dish and pipetted the cell suspension up and down to mix them well. The cell suspension was examined by inverted phase contrast microscope to make sure cells were separated into a single cell suspension. We transferred the cell suspension to a 10 mL-tube and centrifuged it to separate cell pellet from the medium. The cells were washed twice in the RPMI 1640 medium by centrifugation at 300×g for 5 min, and then the washed cells were re-suspended in 10 mL of medium. Cell number and viability were determined by using a dye of trypan blue, a special counting chamber, the hemocytometer and microscope. The cell density was calculated by the formula, cell concentration=$(N1+N2+N3+N4+N5) \times 4 \times 10^3$ cells/mL, where N1 to N5 denote the counting numbers in the chamber. The cell suspension was diluted to a final concentration of 100,000 cells/mL in the RPMI 1640 medium.

Assay Plate Set-Up

The cells were initially seeded in a 96-well plate with a cell density of 10,000 cells per well by transferring 100 µL of 100,000 cells/mL suspension to each well using a multi-pipette. The 96-well plate was incubated for 24 hours at 37° C. in a humidified, 5% $CO_2$ atmosphere. After incubation of 24 h, the growth medium was removed and replaced with 100 µL of fresh medium with different concentrations of drugs in 3 repeats.

Treating Cells with Different Concentrations of Drugs

Prepare 3.2 mL of TEMPOL, chlorambucil, TEMPOL+ chlorambucil and chlorambucil-TEMPOL adduct solutions in the growth medium with an original concentration of 3200 µM, respectively. Performed serial two-fold dilution from Row H to Row A. Use extra column as the negative control containing 100 µL of the medium and cells only. Before the drug solutions were administered, removed the growth medium from each well and then replace 100 µL of each drug solution. Each concentration had 3 repeats. Incubate the plate for 72 hours.

Cell Lysis and Supernatant Harvest

10 µL of Lysis Solution was added from row A to H, and incubated for 45 minutes in a humidified chamber at 37° C., under 5% $CO_2$.

LDH Measurement

50 µl supernatant was transferred from all wells to a fresh 96-well flat bottom enzymatic assay plate. Assay buffer solution was thawed and 12 ml of assay buffer solution was warmed to room temperature. It was then added to a bottle of substrate mixture. 50 µl/well of reconstituted substrate mix was added to each well of the enzymatic plate, and it was covered with foil to protect from light, and the cells were incubated at room temperature for 30 minutes. 50 µl Stop Solution was added to each well, and the absorbances were recorded at a wavelength of 490 nm within one hour after adding the stop solution. The assay procedure can be summarized as seen in Appendix 1-7.

Results

We have measured the number of dead cells that are directly proportional to the absorbance recorded. Hence as the concentration of drug increases, the number of dead cells increases. Graphs in Appendix 1-8 reveal that under same conditions and at same concentrations, chlorambucil-TEMPOL adduct has the most % cytotoxicity, the physical mixture of chlorambucil+TEMPOL the second, chlorambucil the third and TEMPOL the least. TEMPOL itself shows very low % cytotoxicity under similar conditions, however, when mixed physically with chlorambucil or bound to chlorambucil by chemical reaction, synergizes the potency of chlorambucil. This may be due to apoptosis that occurs via free radical mechanism induced by TEMPOL. TEMPOL is able to exert cyto-protective or cyto-toxic effects. Such dual behavior is not uncommon among antioxidants. TEMPOL has been found to target the mitochondrion with subsequent impairment of the electron transport chain via free radical mechanism. Also, TEMPOL has been found to induce apoptosis in different types of cancer cells due to ceramide generation. Nitroxide TEMPOL and TEMPO stimulate distinct signal transduction pathways maybe triggered by secondary radicals associated with cellular metabolism and differentially regulated by early events, such as control of protein tyrosine phosphorylation and generation of ceramide. The chlorambucil-TEMPOL adduct may allow chlorambucil to act via alkylation, while at the same time TEMPOL acts via free radical mechanism due to the proximity of the two functional groups.

Example 9

DNA Experiment

In order to understand the enhanced potency of chlorambucil-TEMPOL adduct at molecular level in causing cell death, we carried out the NMR study of chlorambucil, TEMPOL and chlorambucil-TEMPOL adduct with a short single strand DNA units comprising of 3'-ATCGT-5'. We prepared the samples of DNA-chlorambucil (1:1 molar ratio), TEMPOL-DNA (1:1 molar ratio) and DNA-chlorambucil-TEMPOL adduct (1:1 molar ratio) in DMSO-$d_6$ solvent (dimethyl-$d_6$ sulfoxide). The reason the use the DMSO solvent is that both Chlorambucil, and chlorambucil-TEMPOL were weakly soluble in $D_2O$, and DMSO does not effect the conformation of single stranded DNA. We did the $^1H$ and $^{31}P$ NMR experiments at a 600 MHz NMR spectrometer for all three samples.

The DNA-TEMPOL Sample:

The evidence that TEMPOL interacts with DNA is seen by $^1H$ NMR spectra as shown in Appendix 1-9. In the presence of TEMPOL, the $^1H$ DNA chemical shifts in the region 2-3.5 ppm are broadened. These peaks represent the sugar units of DNA. Greater evidence of the interaction is seen in the region between 4.5-5 ppm, where the two doublets (dd) of the blank DNA spectrum are less separated in the presence of TEMPOL. Although presently, we have not confirmed as to which residue of DNA is interacting with TEMPOL, we can for sure see the changes in $^1H$ chemical shifts of the DNA in the presence of TEMPOL. A larger effect is seen in the $^{31}P$ NMR spectrum of DNA in the existence of TEMPOL for a 1:1 molar ratio sample as shown in Appendix 1-10. Although detailed interpretation of these signals is not available at this moment, we can clearly see the interaction of TEMPOL with the DNA.

The DNA-chlorambucil, sample: Comparison of the NMR spectra in Appendix 1-11 of DNA and DNA-chlorambucil, samples shows the interaction of the alkylating agent with DNA. The $^1H$ peak of the Thymine $CH_3$ at 1.8 ppm for the DNA-chlorambucil, sample is strongly affected and forms a doublet (a) compared with the singlet peak for the DNA sample. Spectral changes also occur for the peaks corresponding to the H1' and H2' of the sugar units at 6-6.5 ppm (b) and 2-2.5 ppm (a), respectively. The $^{31}P$ signal of DNA also had a change in chemical shift in the presence of chlorambucil, compared with the spectrum of the native DNA, as shown in Appendix 1-12.

The DNA-chlorambucil-TEMPOL adduct sample: The peaks in the $^1H$ NMR spectrum of the DNA-chlorambucil-TEMPOL adduct sample, shown in Appendix 1-13, look broader compared with those of the DNA-chlorambucil, peaks, showing the effect of TEMPOL group in interaction with the DNA besides the major interaction of the chlorambucil, part with the DNA. The $^{31}P$ spectrum of the DNA-chlorambucil-TEMPOL adduct sample, shown in Appendix 1-14, also shows the change of the peak intensities and linewidths compared with the spectrum of DNA-chlorambucil, sample. The comparisons of the spectra of the DNA-chlorambucil-TEMPOL adduct sample with those of the DNA-chlorambucil, sample reveal that the N-alkyl group in chlorambucil, and the nitroxide group in TEMPOL interact with the DNA collaboratively. This could be related to the enhanced potency of chlorambucil-TEMPOL adduct as compared to the native chlorambucil to cause cell death.

Example 10

Synthesis of Chlorambucil-4-Amino-TEMPO Adduct

In order to show that other derivatives of TEMPO can be used in the preparation of the adduct, as an example, we carried out the reaction of chlorambucil with 4-Amino-TEMPO to give the corresponding amide as the final product. A similar method as described in the synthesis route of the chlorambucil-TEMPOL adduct was used, the only change being, that instead of TEMPOL, 4-Amino-TEMPO (Mol. Wt. 171.26) was used. The final product was analyzed by TLC and characterized by EPR and Maldi-TOF.

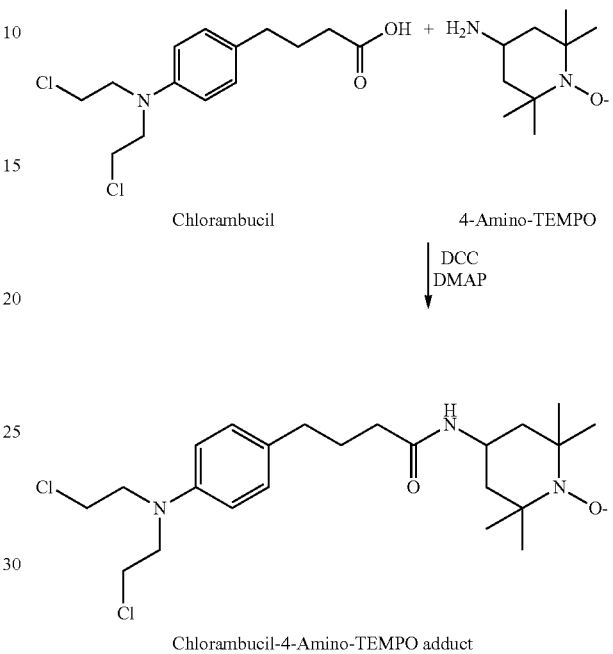

Example 11

Characterization of Chlorambucil-4-Amino-TEMPO Adduct—EPR

As in the previous case, the operating frequency of the spectrometer is 9.7 GHz. Typical scans included 16 scans at a center field of 3318 G and a sweep width of 100 G. The chlorambucil-4-Amino-TEMPO adduct and the 4-Amino TEMPO samples were analyzed at concentrations of $2\times10^{-6}M$ in methylene chloride solvent. The free radical group was left intact as the compound showed a hyperfine triplet in the EPR spectrum, as shown in Appendix 1-15.

Example 12

Characterization of Chlorambucil-4-Amino-TEMPO Adduct—Mass Spectrometry

Similar techniques and protocols as those in the analysis of the chlorambucil-TEMPO adduct, were used in the Maldi-TOF analysis shown in Appendix 1-16. The molecular weight of the chlorambucil-4-Amino-TEMPO adduct is 457.47 a.m.u. The peak at 458.1875 corresponds to the product, or the M+1 ion of the product as the —NH group was protonated by the matrix. This example shows that we can successfully synthesize the analogues of the spin labeled antineoplastic agents using different derivatives of the starting materials.

APPENDIX 1 – ANALYTICAL DATA
1-1
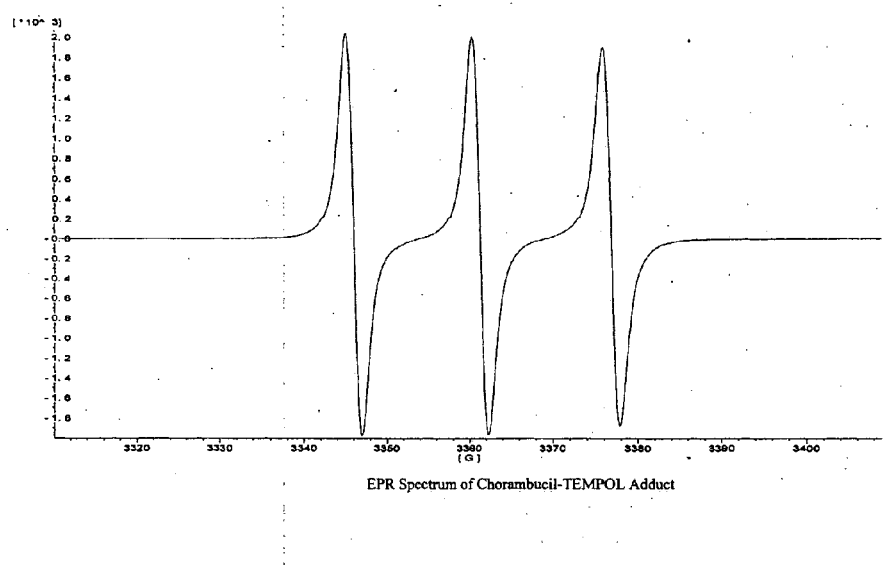
EPR Spectrum of Chorambucil-TEMPOL Adduct 1-2
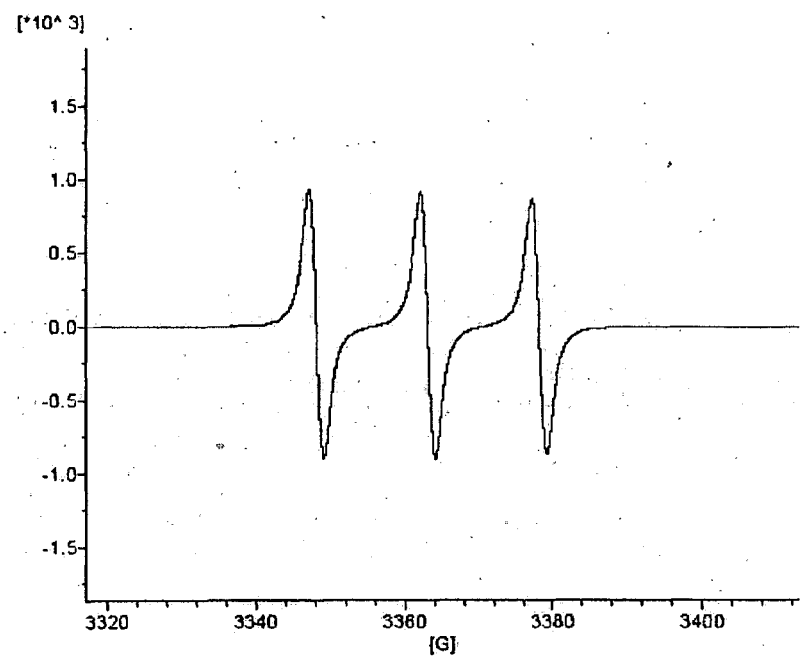
EPR Spectrum of TEMPOL 1-3
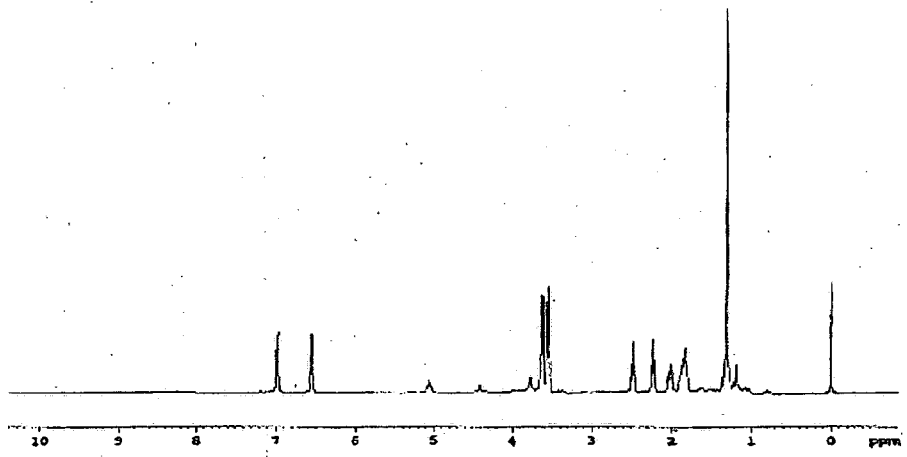
$^1$H NMR signal for the Chlorambucil-TEMPOL adduct in CDCl$_3$ solvent referenced with TMS to 0 ppm at 299.3 K.

1-4
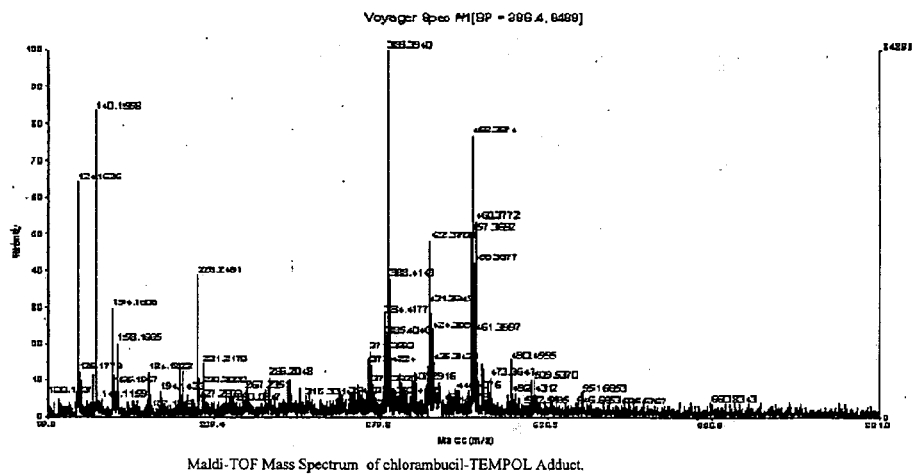
Maldi-TOF Mass Spectrum of chlorambucil-TEMPOL Adduct.

1-5
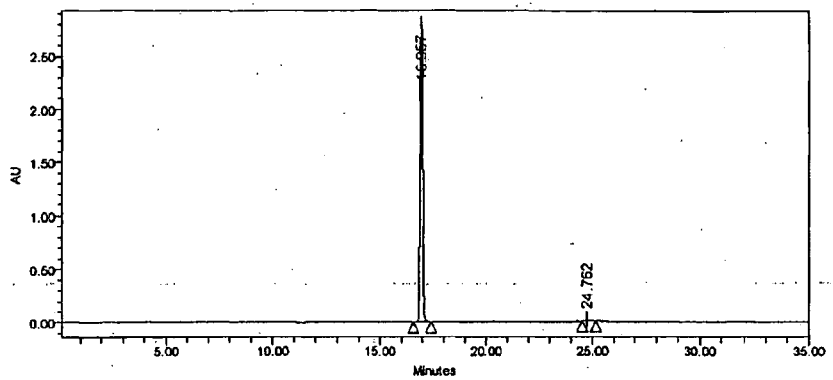
HPLC chromatogram of TEMPOL at 254 nm for the PDA detector.
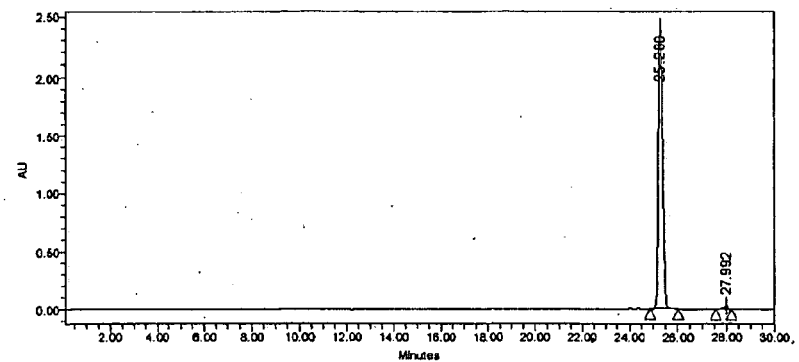
HPLC chromatogram of chlorambucil at 254 nm for the PDA detector.
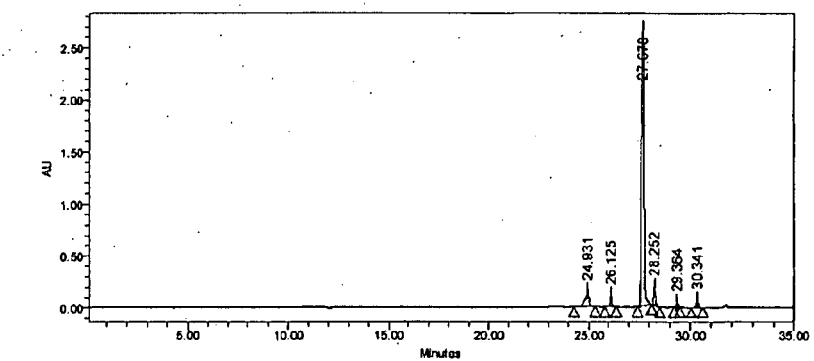
HPLC chromatogram of chlorambucil-TEMPOL at 254 nm for the PDA detector.

1-6
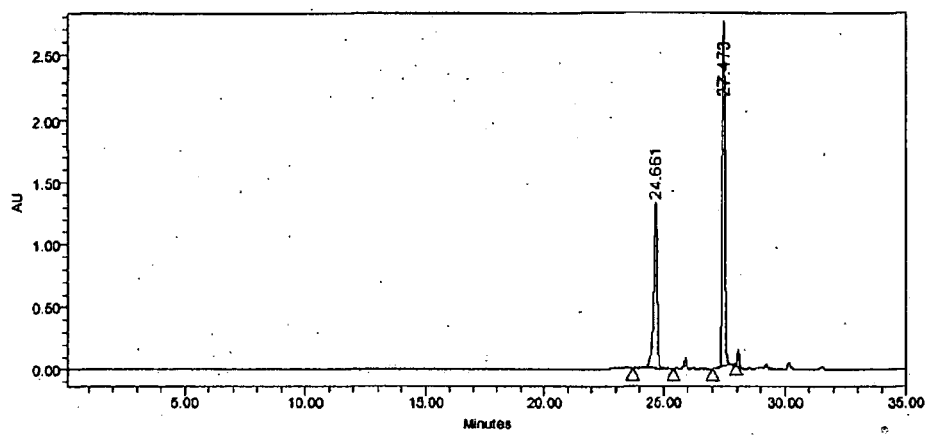
HPLC chromatogram of CT + Chlorambucil co-injection at 254 nm for the PDA detector.

1-7
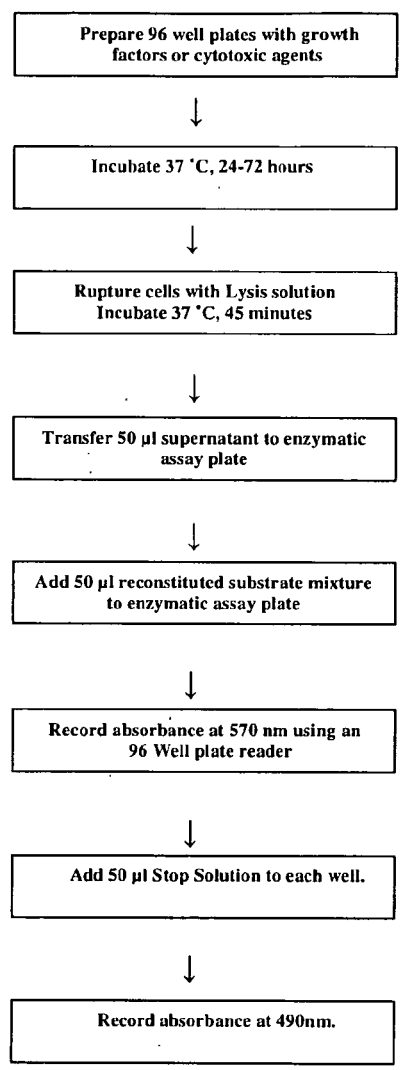

1-8
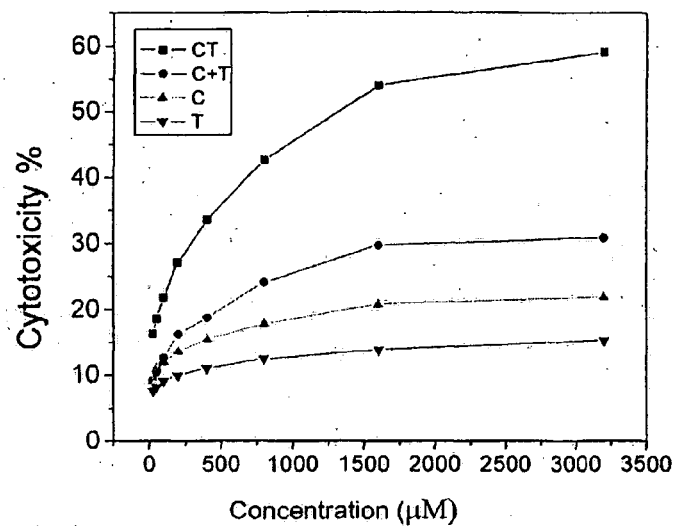
Cytotoxicity of chlorambucil-TEMPOL adduct to MCF-7 cells
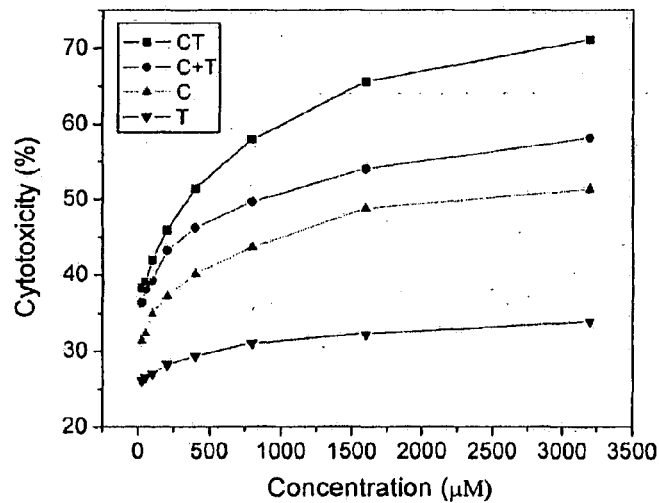
Cytotoxocity of chlorambucil-TEMPOL adduct to KB cells 1-9
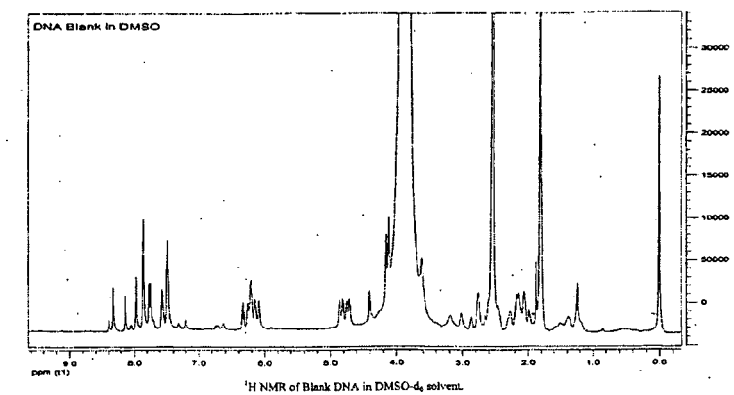
¹H NMR of Blank DNA in DMSO-d₆ solvent.
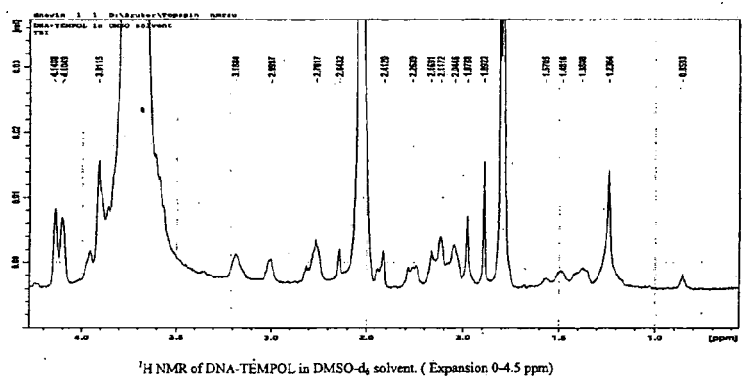
¹H NMR of DNA-TEMPOL in DMSO-d₆ solvent. (Expansion 0-4.5 ppm)
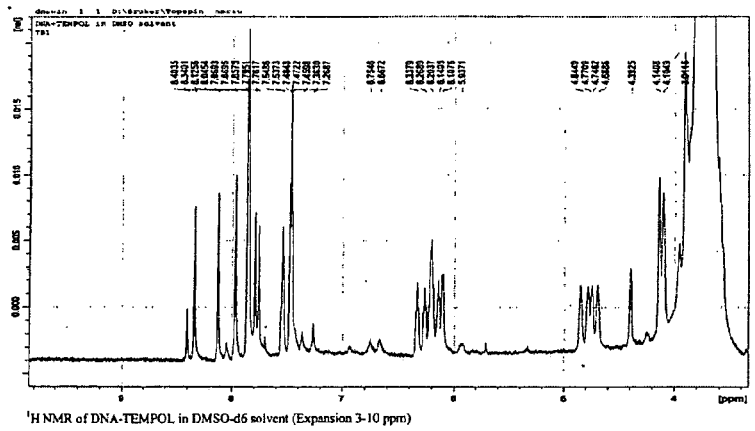
¹H NMR of DNA-TEMPOL in DMSO-d6 solvent (Expansion 3-10 ppm)

1-10
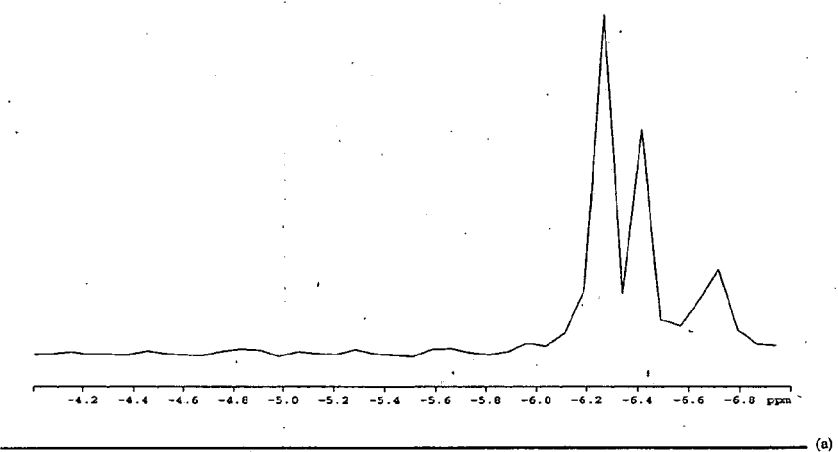
(a)
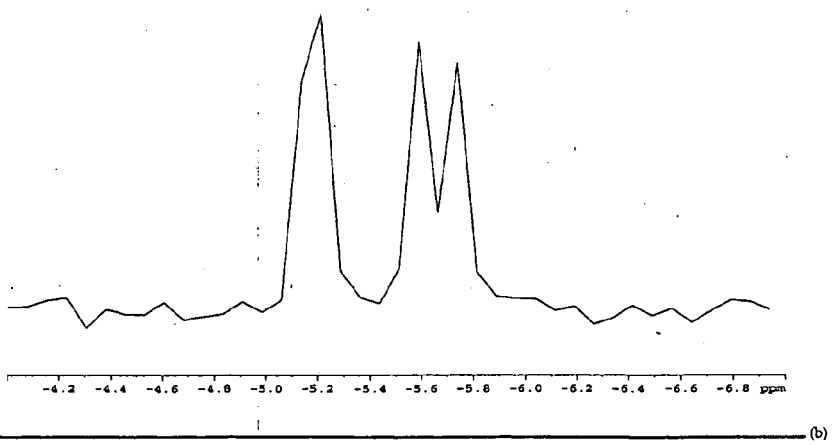
(b)
$^{31}$P NMR spectra of (a) DNA, and (b) DNA in the presence of TEMPOL, showing the effect of TEMPOL in interaction with DNA.

1-11
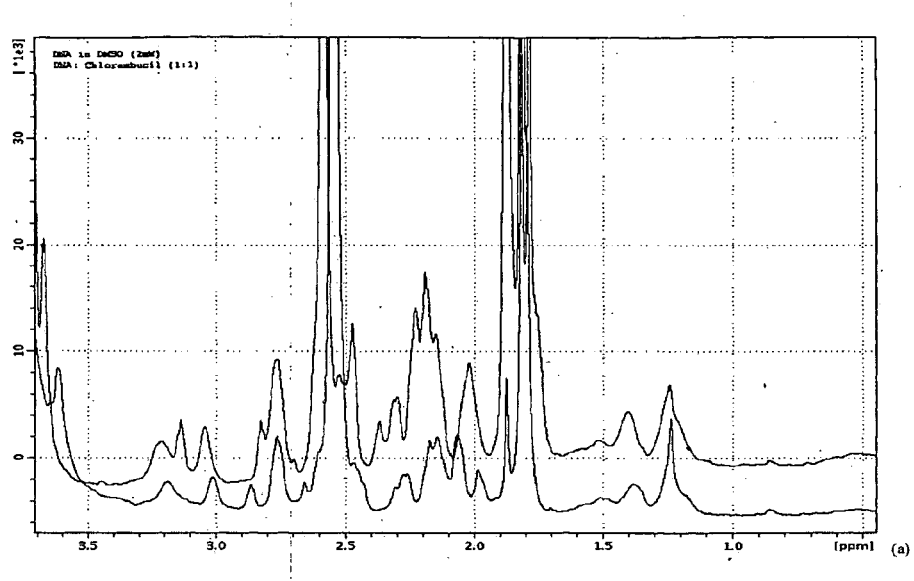
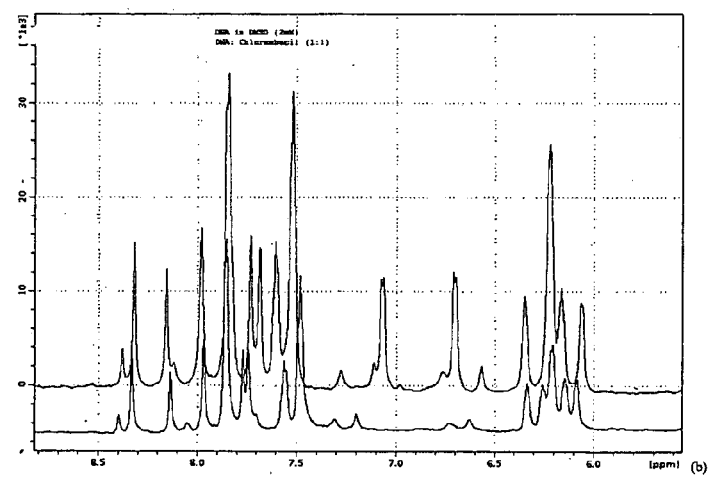
¹H NMR spectra of DNA (blue) and DNA in the existence of chlorambucil (red). Spectra (a) and (b) show the different regions. Changes in the ¹H NMR chemical shift of DNA in the presence of chlorambucil are obvious.

1-12
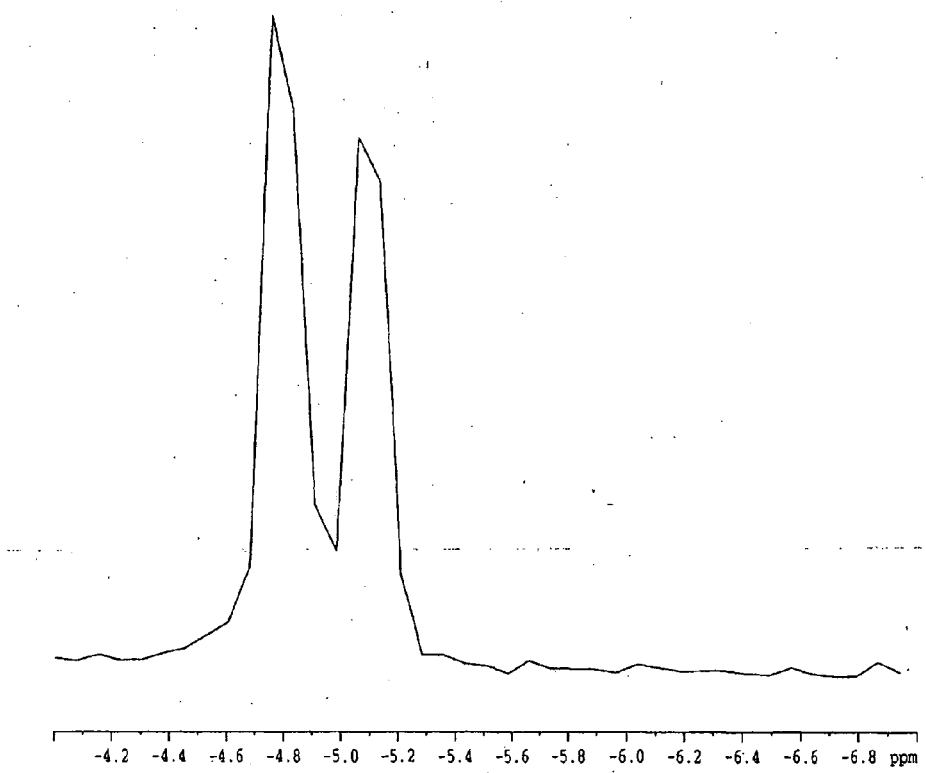
$^{31}$P NMR of DNA in the presence of chlorambucil. The change is obvious compared with the $^{31}$P spectrum of the native DNA.

1-13
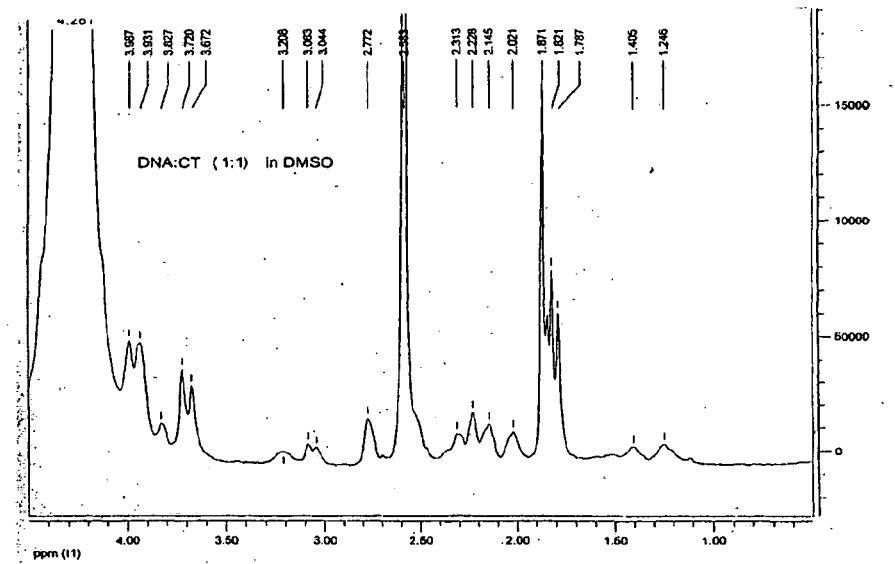
¹H NMR spectra of DNA in the presence of chlorambucil-TEMPOL adduct. Effect of chlorambucil-TEMPOL adduct on the DNA is marked by the broadening of signals in the 2-3.5ppm region compared with those of for the DNA- chlorambucil, spectra.

1-14
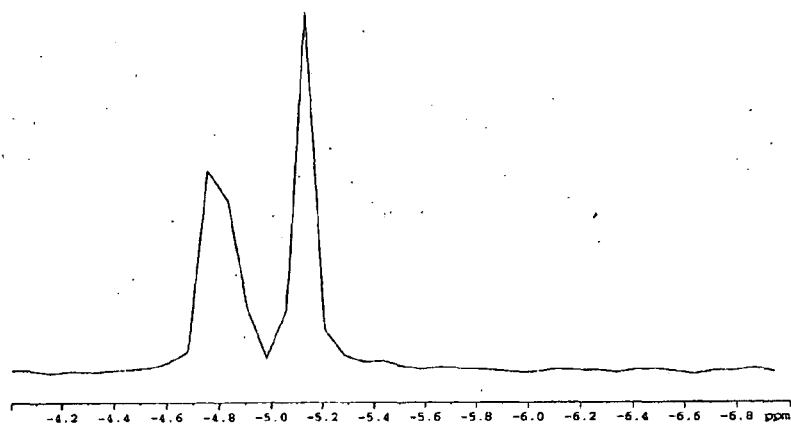
$^{31}$P NMR of DNA in the presence of chlorambucil-TEMPOL adduct. It shows the difference when compared with that of DNA in the presence of chlorambucil.

1-15
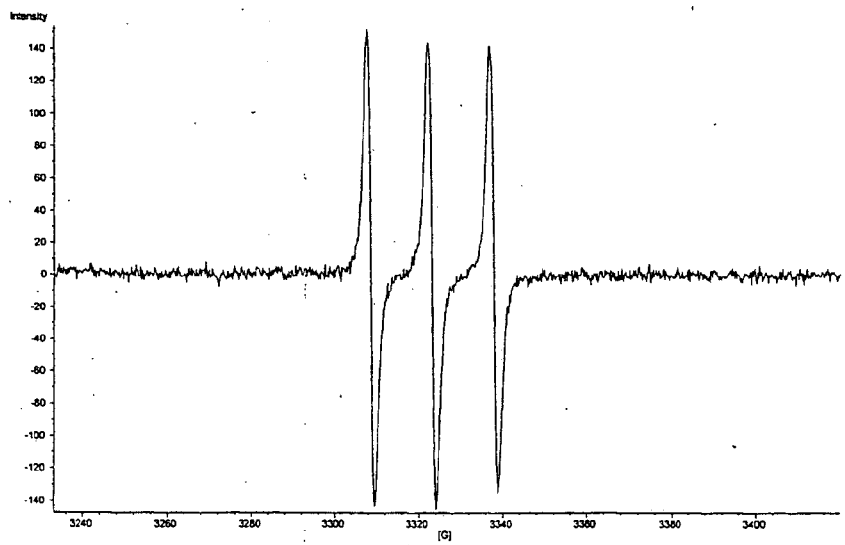
EPR Spectrum of chorambucil-4-Amino-TEMPO Adduct
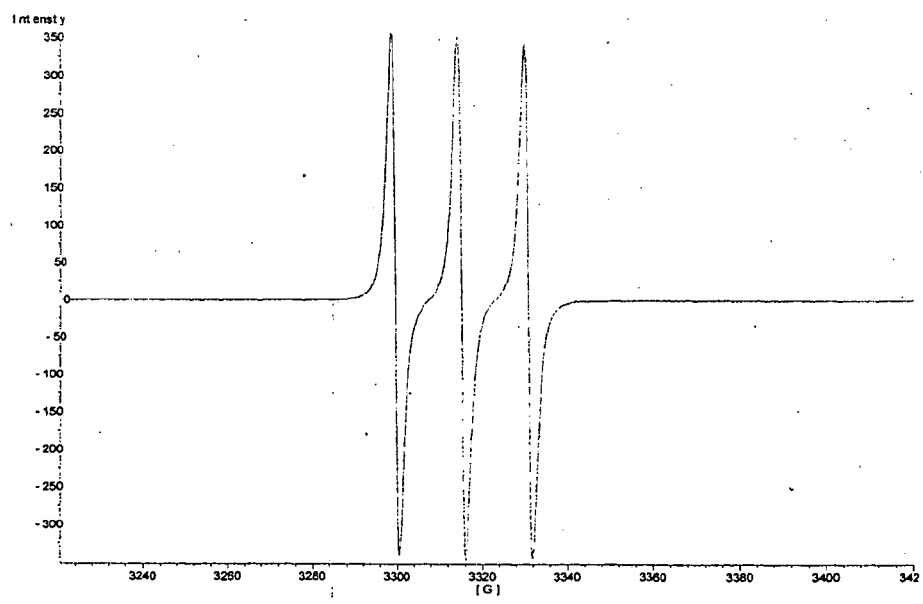
EPR Spectrum of 4-Amino-TEMPO 1-16
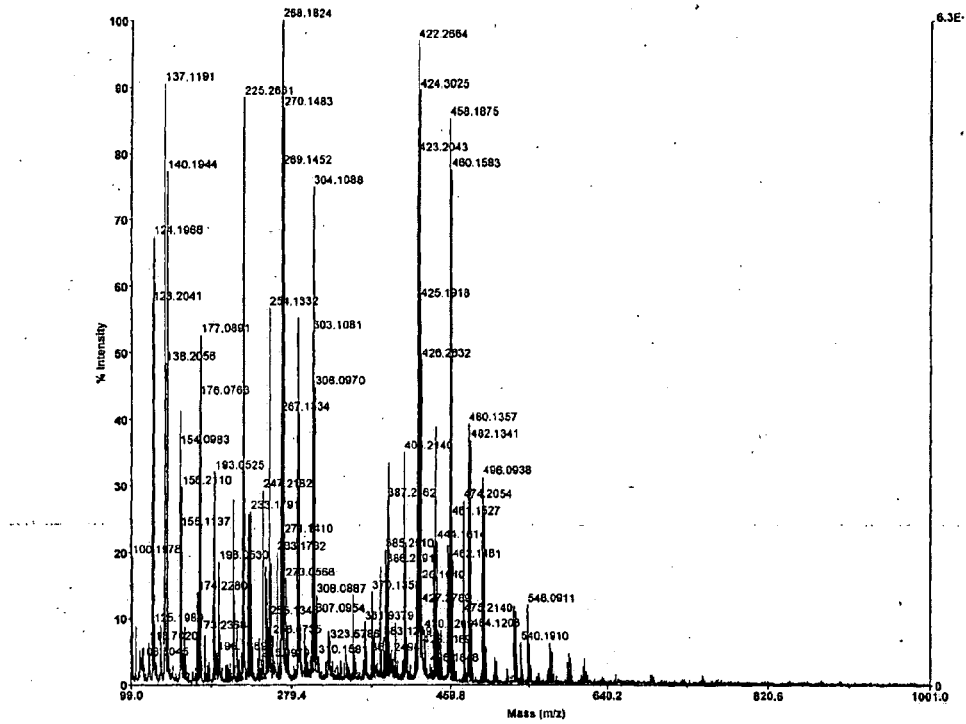
Maldi-TOF Mass Spectrum of chlorambucil-4-Amino-TEMPO

The invention claimed is:

1. A compound having the formula

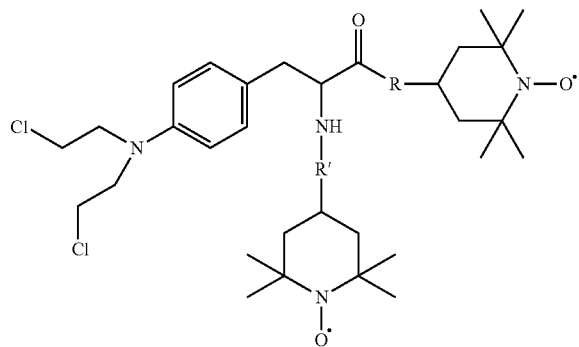

wherein R=O or NH; and R'=CO.

2. A compound having the formula

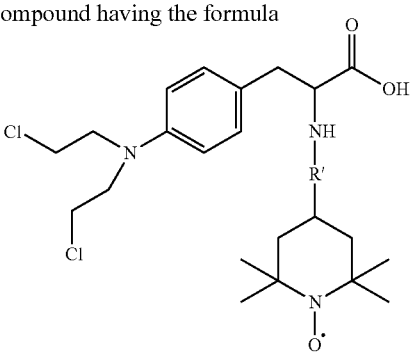

wherein R'=CO.

3. A method for increasing the effectiveness of a chlorambucil anticancer agent comprising a —CO functional group, comprising forming an adduct with the chlorambucil anticancer agent or a derivative thereof and at least one compound selected from the group consisting of TEMPO, TEMPO derivatives, their precursors, and combinations thereof.

4. The method of claim 3 wherein the adduct is formed via at least one covalent bond.

5. A method for increasing the effectiveness of a melphalan anticancer agent comprising a —CO functional group, comprising forming an adduct with the melphalan anticancer agent or a derivative thereof and at least one compound selected from the group consisting of TEMPO, TEMPO derivatives, their precursors, and combinations thereof.

6. The method of claim 5 wherein the adduct is formed via at least one covalent bond.

* * * * *